(12) United States Patent
Schneider

(10) Patent No.: US 8,277,458 B2
(45) Date of Patent: Oct. 2, 2012

(54) APPARATUS AND METHOD FOR ARTHROSCOPIC TRANSHUMERAL ROTATOR CUFF REPAIR

(75) Inventor: David J. Schneider, Lafayette, CO (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 673 days.

(21) Appl. No.: 12/358,953

(22) Filed: Jan. 23, 2009

(65) Prior Publication Data

US 2010/0191247 A1 Jul. 29, 2010

(51) Int. Cl.
*A61B 17/58* (2006.01)
*A61B 17/60* (2006.01)
*A61F 2/00* (2006.01)

(52) U.S. Cl. .................................... 606/96; 606/86 R

(58) Field of Classification Search .............. 606/96, 606/86 R, 87, 88; 623/19.11–19.14
See application file for complete search history.

(56) References Cited

U.S. PATENT DOCUMENTS

| | | |
|---|---|---|
| 3,345,989 A | 10/1967 | Reynolds |
| 3,353,539 A | 11/1967 | Preston |
| 3,421,512 A | 1/1969 | Frasier |
| 3,749,101 A | 7/1973 | Williamson |
| 3,842,843 A | 10/1974 | Mourot et al. |
| 3,897,267 A | 7/1975 | Tseung et al. |
| 4,195,367 A | 4/1980 | Kraus |
| 4,216,548 A | 8/1980 | Kraus |
| 4,652,459 A | 3/1987 | Engelhardt |
| 4,932,951 A | 6/1990 | Liboff et al. |
| 4,937,323 A | 6/1990 | Silver et al. |
| 5,067,940 A | 11/1991 | Liboff et al. |
| 5,112,337 A | 5/1992 | Paulos et al. |

(Continued)

FOREIGN PATENT DOCUMENTS

DE 4233605 6/1994

(Continued)

OTHER PUBLICATIONS ezLoc Femoral Dixation Device, Bioment Sports Medicine, 2007, pp. 1-12.

(Continued)

*Primary Examiner* — Kevin T Truong
*Assistant Examiner* — Olivia C Chang
(74) *Attorney, Agent, or Firm* — Harness, Dickey

(57) ABSTRACT

Apparatuses and methods are provided for arthroscopic rotator cuff repair incorporating a transhumeral bone tunnel. The apparatus comprises a number of components that can also be considered a repair system to include a drill guide, a marking hook, and a drill with a removable tip that serves as a bone anchor. In another aspect, the invention provides a suture especially adapted for securing both soft tissue and bone anchors that reduces forces transmitted to the anchors by secondary anchoring of the suture within the bone tunnel based on the geometry of the anchor. In additional aspects of the invention, the components of the drill guide assembly comprise a cannulated marking hook and a drill guide with multiple bores. In additional aspects of the invention, an implantable bone anchor is provided that is especially adapted for placement through a bone tunnel, and wherein the implantable anchor is collapsible to increase the effective size of the anchor for securing the anchor to the far side opening of the bone tunnel through which the anchor was placed. Methods of the invention include a method of arthroscopic repair of a rotator cuff, and methods of activating an implantable anchor.

21 Claims, 9 Drawing Sheets

U.S. PATENT DOCUMENTS

| | | |
|---|---|---|
| 5,123,898 A | 6/1992 | Liboff et al. |
| 5,195,542 A | 3/1993 | Gazielly et al. |
| 5,292,252 A | 3/1994 | Nickerson et al. |
| 5,306,278 A | 4/1994 | Dahl et al. |
| 5,350,383 A | 9/1994 | Schmieding et al. |
| 5,353,935 A | 10/1994 | Yeager et al. |
| 5,383,935 A | 1/1995 | Shirkhanzadeh |
| 5,395,382 A | 3/1995 | DiGiovanni et al. |
| 5,433,735 A | 7/1995 | Zanakis et al. |
| 5,441,508 A | 8/1995 | Gazielly et al. |
| 5,458,558 A | 10/1995 | Liboff et al. |
| RE35,129 E | 12/1995 | Pethica et al. |
| 5,575,801 A | 11/1996 | Habermeyer et al. |
| 5,681,333 A | 10/1997 | Burkhart et al. |
| 5,725,377 A | 3/1998 | Lemler et al. |
| 6,013,083 A | 1/2000 | Bennett |
| 6,019,781 A | 2/2000 | Worland |
| 6,206,886 B1 | 3/2001 | Bennett |
| 6,214,049 B1 | 4/2001 | Gayer et al. |
| 6,409,764 B1 | 6/2002 | White et al. |
| 6,514,274 B1 | 2/2003 | Boucher et al. |
| 6,616,665 B2 | 9/2003 | Grafton et al. |
| 6,778,861 B1 | 8/2004 | Liebrecht et al. |
| 6,828,908 B2 | 12/2004 | Clark |
| 6,830,572 B2 | 12/2004 | Mcdevitt et al. |
| 7,004,974 B1 | 2/2006 | Larsson et al. |
| 7,172,594 B2 | 2/2007 | Biscup |
| 7,230,153 B2 | 6/2007 | Flick |
| 7,938,847 B2 | 5/2011 | Fanton et al. |
| 2004/0199166 A1 | 10/2004 | Schmieding et al. |
| 2006/0078847 A1 | 4/2006 | Kwan |
| 2006/0100629 A1 | 5/2006 | Lee |
| 2006/0155384 A1 | 7/2006 | Ellingsen et al. |
| 2006/0247641 A1 | 11/2006 | Re et al. |
| 2007/0198087 A1 | 8/2007 | Coleman et al. |
| 2007/0233128 A1* | 10/2007 | Schmieding et al. ........... 606/79 |
| 2008/0015578 A1 | 1/2008 | Erickson et al. |
| 2009/0105753 A1* | 4/2009 | Greenhalgh et al. .......... 606/228 |
| 2010/0292756 A1 | 11/2010 | Schneider |

FOREIGN PATENT DOCUMENTS

EP 2409656 A1 1/2012

OTHER PUBLICATIONS

Fleega, "Arthroscopic Transhumeral Rotator Cuff Repair: Giant Needle Technique", Arthroscopy Feb. 2002, 18(2):218-23.

Gonzalez-Lomas et al., "In situ transtendon repair outperforms tear completion and repair for partial articular-sided supraspinatus tendon tears", J Shoulder Elbow Surg 2008; 17:722-728.

Kim et al., "Arthroscopic Transosseous Rotator Cuff Repair", Orthopedics 2008, 31:327-30.

Meyer et al., "Association of osteopenia of the humeral head with full-thickness rotator cuff tears", JSES 2004: 13:333-7, Zurich and Bassersdorf, Switzerland.

Jiang, "Bioelectric Battery and Its Application", St. Jude Medical, Dec. 13, 2007.

Locking Compression Plate (LCP) System, Synthes North America, 2009, available at http://us.synthes.com/Products/Trauma/Plate+and+Screw+Systems/Locking+Compression+Plate+%28LCP%29+System.htm, accessed Jun. 8, 2009, 1 page.

Partial Search Report for European Patent Application No. 10170339.5, dated Dec. 3, 2010.

U.S. Appl. No. 12/464,705, filed May 12, 2009, Schneider.

Locking Compression Plate (LCP) System, Synthes North America, 2009, available at http://us.synthes.com/Products/Trauma/Plate+and+Screw+Systems/Locking+Compression+Plate+%28LCP%29+System.htm, accessed Jun. 8, 2009, 1 page.

European Search Report for EP Patent Application No. 10170339.5 mailed Mar. 22, 2011.

\* cited by examiner

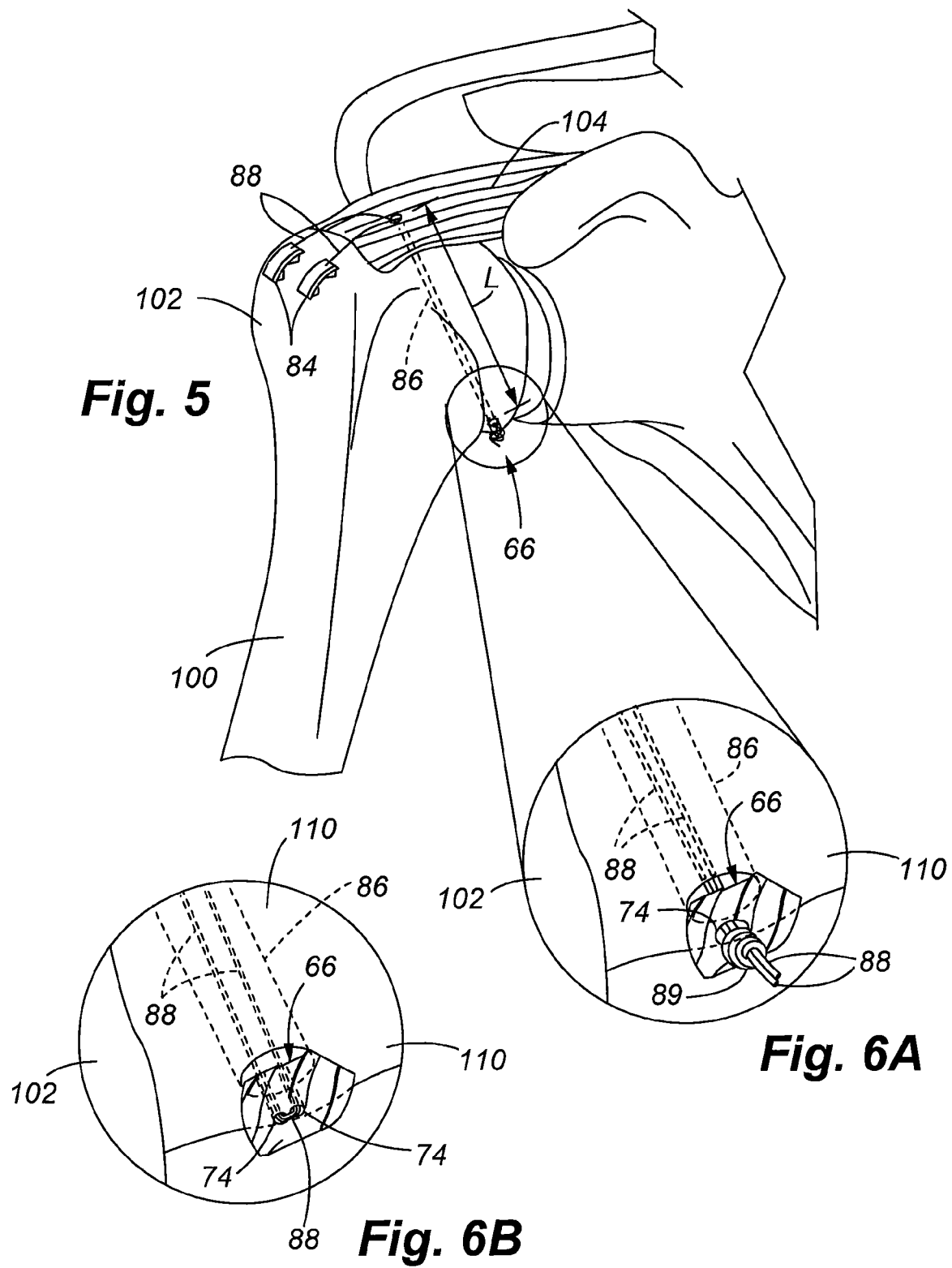

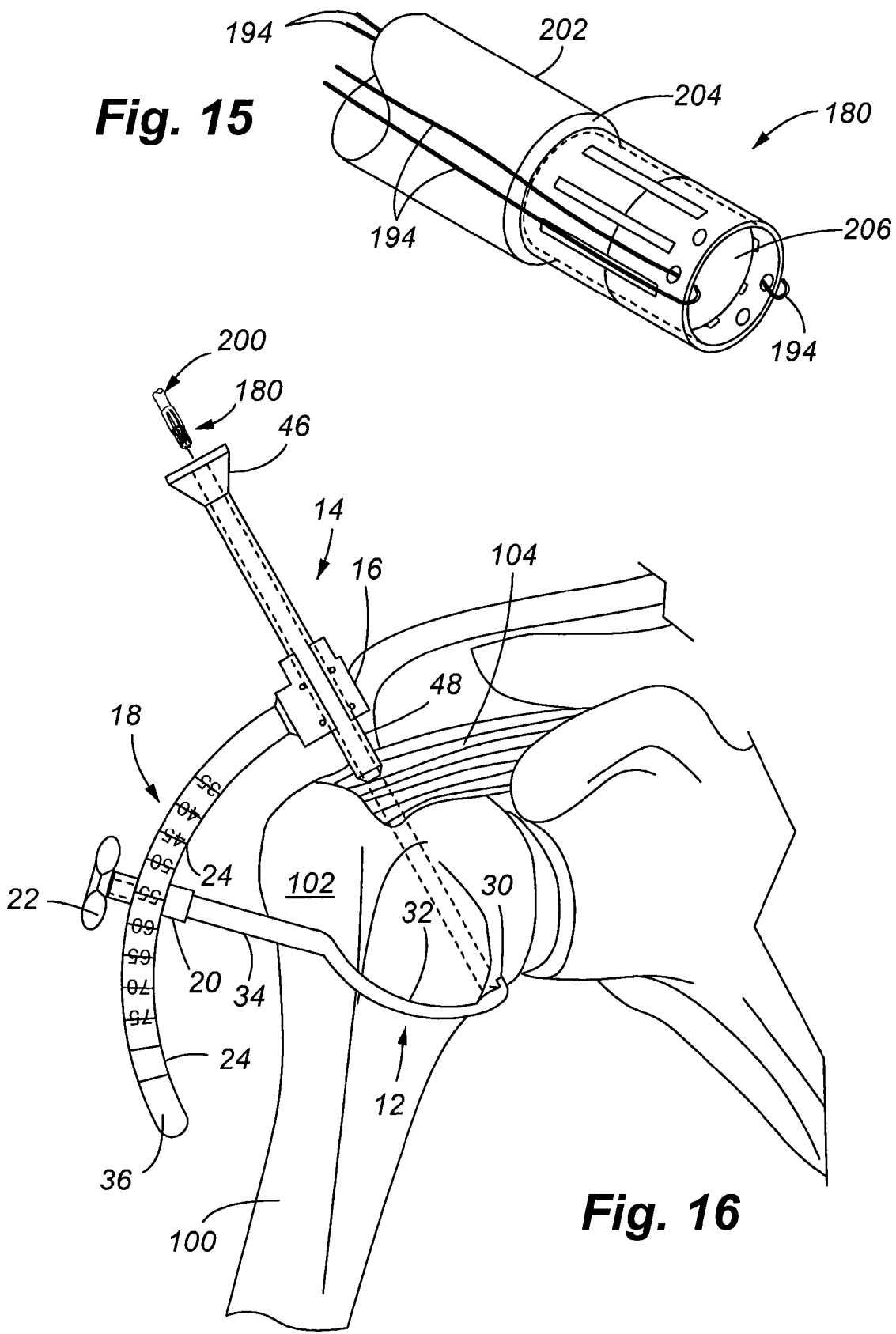

Fig. 20
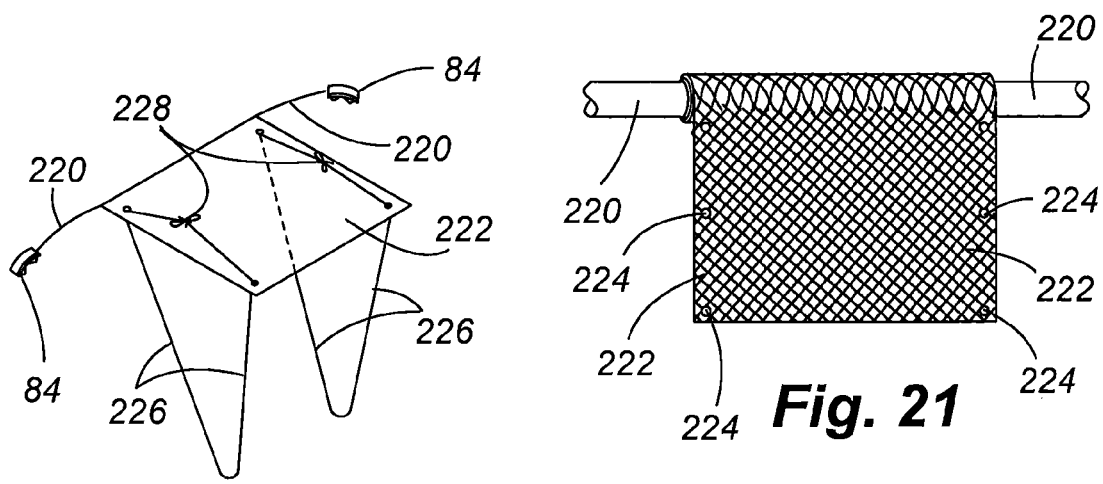
Fig. 22　　Fig. 21
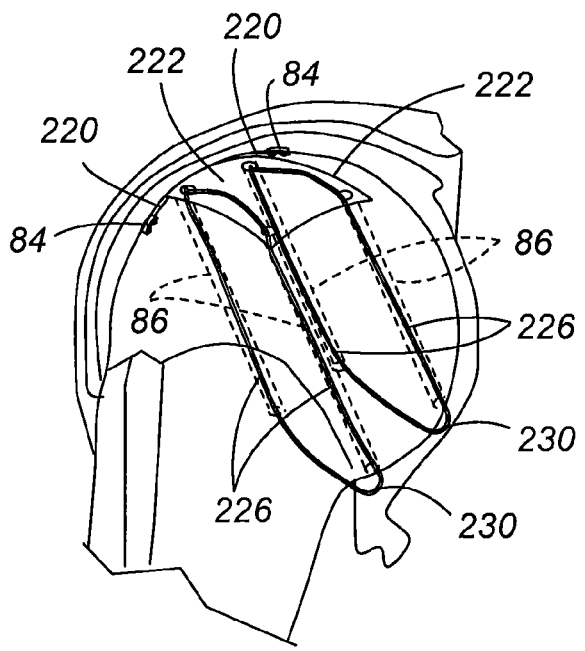
Fig. 23

APPARATUS AND METHOD FOR ARTHROSCOPIC TRANSHUMERAL ROTATOR CUFF REPAIR

FIELD OF THE INVENTION

The present invention relates to surgical devices and methods for repair of torn tissue, and more particularly, to an apparatus and method for repair of a damaged rotator cuff by transhumeral suture anchoring in an arthroscopic procedure.

BACKGROUND OF THE INVENTION

Rotator cuff injuries are a very common injury suffered by patents of all ages. A torn rotator cuff typically requires a surgical procedure to reattach the torn tendons to the bone of the humeral head. Rotator cuff injuries are particularly bothersome in that the torn tendons must be highly stabilized in order for healing to occur.

In recent years, the preferred solution to ensure proper healing of a rotator cuff is to increase the number of anchors used to secure the torn tissue to the bone. Although increasing the number of anchors used in the procedure can result in improved healing, there are also a number of drawbacks associated with the increased use of anchors, most notably, the cost of the procedure.

One known prior art surgical technique for repair of a rotator cuff is the use of a plurality of suture anchor screws that are placed in the head of the humerus bone. The sutures are then threaded through the anchor screws and are passed through the rotator cuff tissue and overlying musculature, resulting in a web of suture strands that are tied to one another thereby reattaching the rotator cuff to the humerus head. One particular disadvantage with this known type of rotator cuff repair is that the plurality of screws is secured within the cancellous bone mass beneath the near cortex of the head of the humerus. This bone mass in the humerus head is particularly susceptible to osteopenic degradation in which the bone density can significantly diminish, particularly in older patents. Accordingly, anchors placed in this degraded cancellous bone mass do not remain stationary, and some degree of pullout or loosening will occur, thereby preventing proper healing of the tendon tissue to the bone.

Two references that disclose apparatuses and methods of rotator cuff repair that do not locate the anchors within the cancellous bone mass of the humeral head are the U.S. Pat. Nos. 6,013,083 and 6,206,886 to Bennett. These references disclose a method wherein a bone tunnel is formed completely through the humeral head extending to the far cortex. An anchor is located at the far cortex within the bone tunnel and sutures are attached to the anchor and extend through the bone tunnel. More specifically, these references disclose an apparatus and method wherein a cannula is inserted through the skin substantially to the torn tissue. A drill guide is inserted in the cannula, a drill bit is inserted in the drill guide, and a hole is then drilled through the torn tissue and completely through the humeral head. The drill bit is removed and an inner cannula is passed through the drill guide until its distal end is engaged in the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool. The deployment tool is passed through the inner cannula and drilled hole until the expandable wings clear the far end of the hole a sufficient distance to allow the wings to expand to a diameter larger than the diameter of the drilled hole. The deployment tool, inner cannula, drill guide, and cannula are removed and tension is applied to the sutures to engage the expanded wings of the anchor on the exterior surface of the bone surrounding the drilled hole. A button is run down the sutures through the cannula and secured on the torn tissue by the sutures such that the torn tissue is secured to the bone and the sutures are anchored to the hard exterior surface of the bone by the expanded anchor.

It is also known within arthroscopic procedures to provide a drill guide in order to selectively drill a tunnel through bone in a precise, directed manner such that the bone tunnel can be used to pass sutures to an anchor located on the far end of the tunnel. Two known references that disclose drill guides for drilling tunnels in the tibia for replacement or repair of knee tendons include the U.S. Pat. Nos. 5,112,337 and 5,350,383.

Although the drill guides of these prior art references are well known for arthroscopic repair of knee tendons, these drill guides have been limited to use with the knee joint, and have not been used as drill guides for other joints.

With respect to repair of a torn rotator cuff, there is still a need to provide an apparatus and method in which the procedure conducted is minimally invasive, minimizes the amount of required hardware, yet is a reliable, repeatable procedure. There is also a need to provide such a procedure in which anchoring of the sutures is achieved by bypassing the cancellous bone mass on the humeral head, and taking advantage of the far cortex of the bone that has a higher density therefore providing a better means to anchor the sutures.

SUMMARY OF THE INVENTION

It is therefore an object of the present invention to provide an apparatus and method for repair of torn rotator cuff tissue wherein sutures are anchored along the far cortex of the bone thereby bypassing the cancellous bone mass.

It is yet another object of the present invention to provide an apparatus and method in which the procedure can be conducted in a minimally invasive manner by minimizing the number of suture passes through the soft tissue, yet ensuring that the sutures are suitably anchored in both a far bone anchor point, as well as a near anchor point in the soft tissue surrounding the rotator cuff.

It is yet another object of the present invention to provide an apparatus and method in which a drill guide can be used to precisely locate bone tunnels to be drilled, and the drill guide is easily adaptable for use with patients of differing sizes.

It is yet another object of the present invention to generally simplify the surgical procedure of a repairing a torn rotator cuff repair in which not only is the amount of implanted hardware reduced, but also the procedure is simplified by minimizing the surgical tools required to conduct the procedure.

It is yet another object of the present invention to provide various suture constructions and suture anchor constructions that facilitate the apparatus and method of the invention.

The above objects and other objects of the invention not specifically articulated are accomplished by the present invention that includes an apparatus and method for repair of torn rotator cuffs.

In accordance with the apparatus of the present invention, a drill guide and drill are provided that are especially adapted for repair of a torn rotator cuff. The drill guide includes a marking hook that is especially adapted for the shape of the humeral head such that a bone/transosseous tunnel can be drilled completely through the humeral head. The drill of the present invention includes a drill bit tip that is used to drill a tunnel through the bone mass, and then serves as the suture anchor. The drill bit tip includes a transverse aperture that can be held by the marking hook, and the drill shaft is then removed from the drill bit tip. The drill bit tip is rotated to extend transversely across the opening formed on the far side of the bone tunnel, and then sutures are passed through the bone tunnel and are secured to the drill bit tip through the aperture of the drill bit tip. The surgeon may then choose the type of soft tissue anchor to be placed on the rotator cuff and musculature surroundings of the rotator cuff. The marking hook can be cannulated as by incorporation of an orifice extending through the marking hook, to thereby allow passage of sutures within the marking hook. After drilling across the humerus, sutures can be passed through the orifice of the marking hook. The suture can then either be passed into the opening of the drill tip or can be grasped by a device placed across the bone/transosseous tunnel.

Also in accordance with the present invention, the method of the present invention contemplates a cortical bone bridge in which two or more bone tunnels can be drilled through the humeral head, and then the sutures can be passed through the bone tunnels in the desired pattern for securing the torn rotator cuff tissue.

In yet another aspect of the present invention, a particularly advantageous self-anchoring suture is provided. This self-anchoring suture incorporates a dispersed pattern of protuberances or beads that can be passed in a specified direction through the bone tunnel but prevent pullout by force applied in the opposite direction.

An additional suture configuration provided to accommodate the transosseous aiming apparatus of the present invention is a suture construction having a mesh-like structure mounted to a conventional suture. The mesh structure is initially rolled tightly around the suture, and then unfurled after the suture ends have been deployed across the humerus and tied along the medial far cortex. The mesh could be a scaffold of any synthetic material or biologic material. The mesh construct could be rolled tightly around the conventional suture, contained in a sleeve, or rolled into place along the body of the conventional suture. The mesh can be provided in various lengths and widths, and would provide "canopy" coverage of the cuff tear. The interface of the canopy and the cuff tendon underneath could be imbued with biologic growth factors or other substances to promote healing.

Another far-cortical anchoring device that can be used with the aiming apparatus of the present invention is a compression fixation anchor that is formed as a cylinder with sutures placed through small holes formed near the distal end of the cylinder. The anchor body has longitudinally extending cuts or slits, and the anchor body is scored circumferentially to allow folding or collapsing of the device at its mid-portion. As the anchor collapses, it becomes much large in circumference. One method of advancing the anchor is to place a nitinol wire through the transosseous tunnel, and then advance the anchor down the nitinol wire in a cannulated fashion while retaining the suture ends. Once the anchor is in the glenohumeral space, tension is applied on the sutures, causing deployment of the wider mid-portion of the anchor. Another method of advancing the anchor is to employ an inserting device through the tunnel in which the anchor is mounted to a distal end of the inserting device. For activation of the anchor, the inserting device can remain engaged with the anchor, the sutures are tensioned, and the anchor deploys as it collapses.

These and other features of the present invention will become more apparent from a review of the following detailed description taken in conjunction with the drawings.

BRIEF DESCRIPTION OF THE DRAWINGS

FIG. 5 is a perspective view of the patient's shoulder area shown also in FIG. 4, illustrating a bone tunnel as drilled by the drill guide assembly, and the drill bit tip being used as an anchor for sutures;

FIG. 6A is a greatly enlarged portion of FIG. 5 illustrating the drill bit tip used as the anchor;

FIG. 6B is another greatly enlarged portion illustrating an alternate suture arrangement for emplacement of the drill bit tip as an anchor;

FIG. 15 is a perspective view of the implantable tool mounted on the emplacement tool;

FIG. 16 is a perspective view of the drill guide assembly and the implantable anchor and emplacement tool prior to insertion within the drill guide;

FIG. 20 is an enlarged perspective view of a suture and mesh usable in the apparatus and method of the present invention;

FIG. 21 is another perspective view of the suture and mesh with the mesh being partially deployed;

FIG. 22 illustrates the suture and mesh combination of FIGS. 20 and 21 as fully deployed, along with additional sutures used through tunnels to secure the mesh; and FIG. 23 is a perspective view of the suture and mesh combination as installed for repair of a rotator cuff injury.

DETAILED DESCRIPTION

Figures 1, 2, 3:
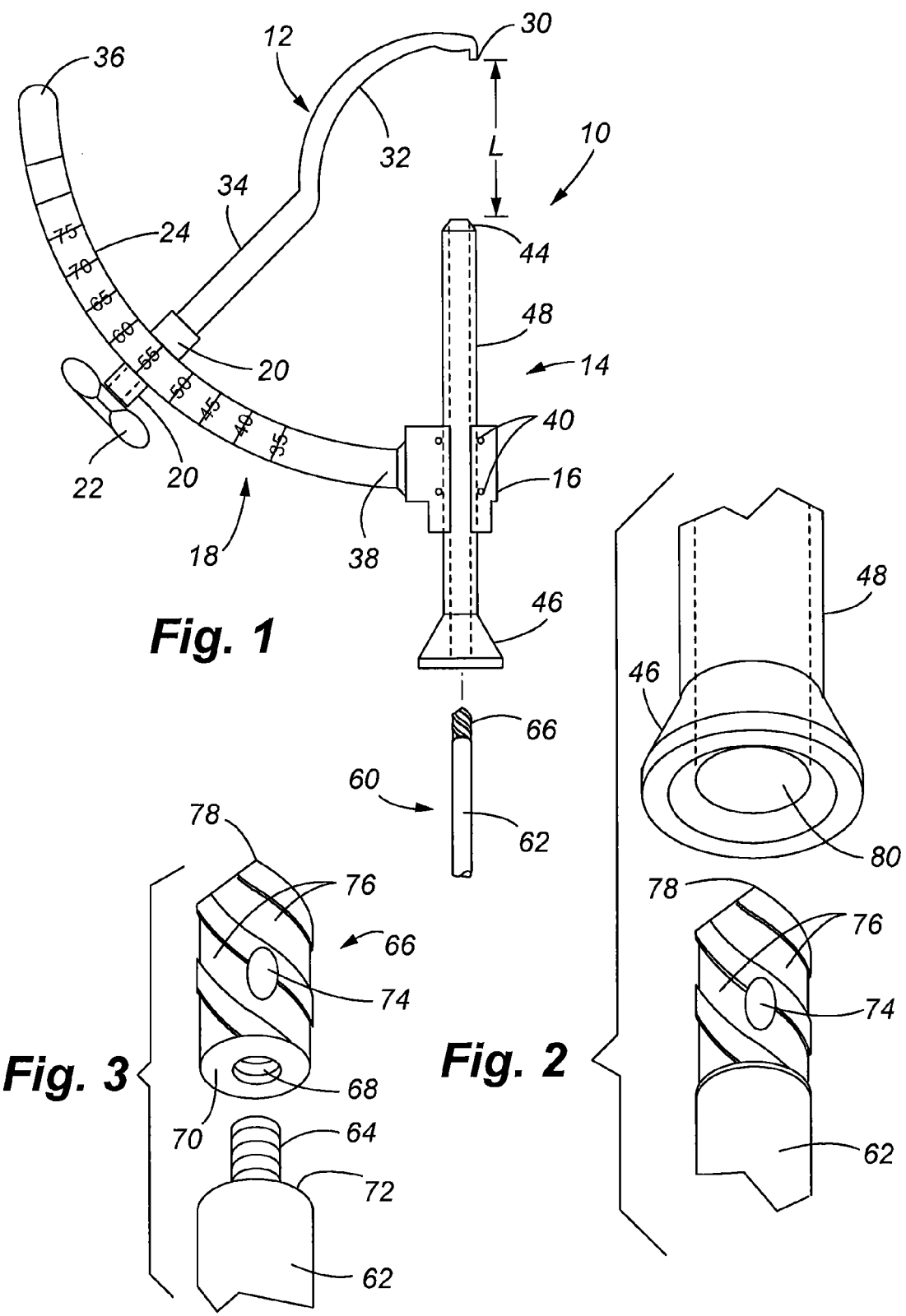
FIG. 1 is a plan view of a drill guide assembly of the present invention.
FIG. 2 is a greatly enlarged fragmentary perspective view of a portion of the drill guide assembly including a bone drill used with the assembly.
FIG. 3 is an enlarged fragmentary exploded perspective view of the bone drill.

Referring to FIG. 1, the drill guide assembly 10 of the present invention is illustrated. The drill guide assembly includes a marking hook 12, a drill guide 14, and an angle setting arm 18. The angle setting arm 18 is secured to one lateral side of a drill guide mount 16. The drill guide 14 is received longitudinally through the drill guide mount 16 and is secured through an open slot in the drill guide mount as by a plurality of set screws 40. The marking hook 12 is secured to the angle setting arm 18 by a marking hook mount 20 which is received at a selected slidable location along the angle setting arm 18. A fastener, such as a wing nut or screw 22 tightens the marking hook mount 20 to a selected angular location along the angle setting arm 18. A plurality of angular gradations 24 are marked along the angle setting arm 18 that assists a practitioner in setting the correct location for the marking hook 12. More specifically, a practitioner must determine the length L of the bone tunnel to be drilled through the humeral head. This length L is defined as the gap between the hook point 30 of the marking hook 12 and the distal end of the drill guide 14. The practitioner also selectively locates the position of the drill guide 14 in terms of how far the distal end of the drill guide extends from the drill guide mount 16.

The marking hook 12 is further characterized by a base 34 that comprises a straight shaft extending from the marking hook mount 20. The distal end of the base transitions into an arcuate extension 32 that is especially adapted to accommodate the curvature of the humeral head. The arcuate extension 32 is especially shaped to accommodate the shape of the humeral head. The radius of curvature of the humeral head ranges from 20 mm to 30 mm. As shown, the extension 32 has a radius R that can be sized in the 20-30 mm range that allows the surgeon to pass the marking hook arthroscopically around the humeral head and onto the bare area of the far cortical bone. The shape of the extension 32 can be defined as an arc or semi-circle that traverses approximately 180 degrees. This uniquely shaped extension is designed specifically for the humeral head which has a shape that is very different from the other joints in the human body. The marking 12 can also have different shapes for right versus left shoulders, thus allowing for passage of the marking hook into the glenohumeral joint along the anterior capsule. FIG. 1 shows the shape of the marking hook 12 as best suited for a right side joint. The hook point 30 extends from the distal tip of the arcuate extension 32 and as shown, the hook point 30 extends in a general direction towards the distal end 44 of the drill guide 14.

Referring also to FIG. 2, the drill guide 14 is characterized as having a shaft 48 with a central bore 80 extending therethrough. The proximal end of the drill guide includes an enlarged portion 46 having an increased internal diameter opening for receiving a bone drill 60.

In accordance with the bone drill 60 of the present invention, it includes a drill shaft 62 and a removable drill bit tip 66. The drill bit tip 66 may have a slightly larger diameter than the drill shaft 62 such that only the drill bit tip 66 cuts through the bone while the drill shaft 62 remains slightly spaced from the bone. The distal end of the drill shaft 62 includes a threaded extension 64 that is inserted within a threaded well 68 of the drill bit tip 66. When the drill bit tip 66 is secured to the drill shaft 62, planar surface 70 of the drill bit tip 66 abuts the facing planar surface 72 of the drill shaft 62.

The particular shape of the drill bit tip 66 is characterized by a plurality of flutes 76 that are formed with a helical pattern on the exterior surface of the drill bit tip 66. The distal tip of the bit tapers to form a generally transverse extending cutting edge 78. The drill bit tip 66 also includes a transverse aperture or opening 74 that extends completely through the tip 66. One acceptable size for the drill bit tip 66 is one that has a diameter of approximately 2.5 mm and is approximately 5.0 mm in length.

Figure 4:
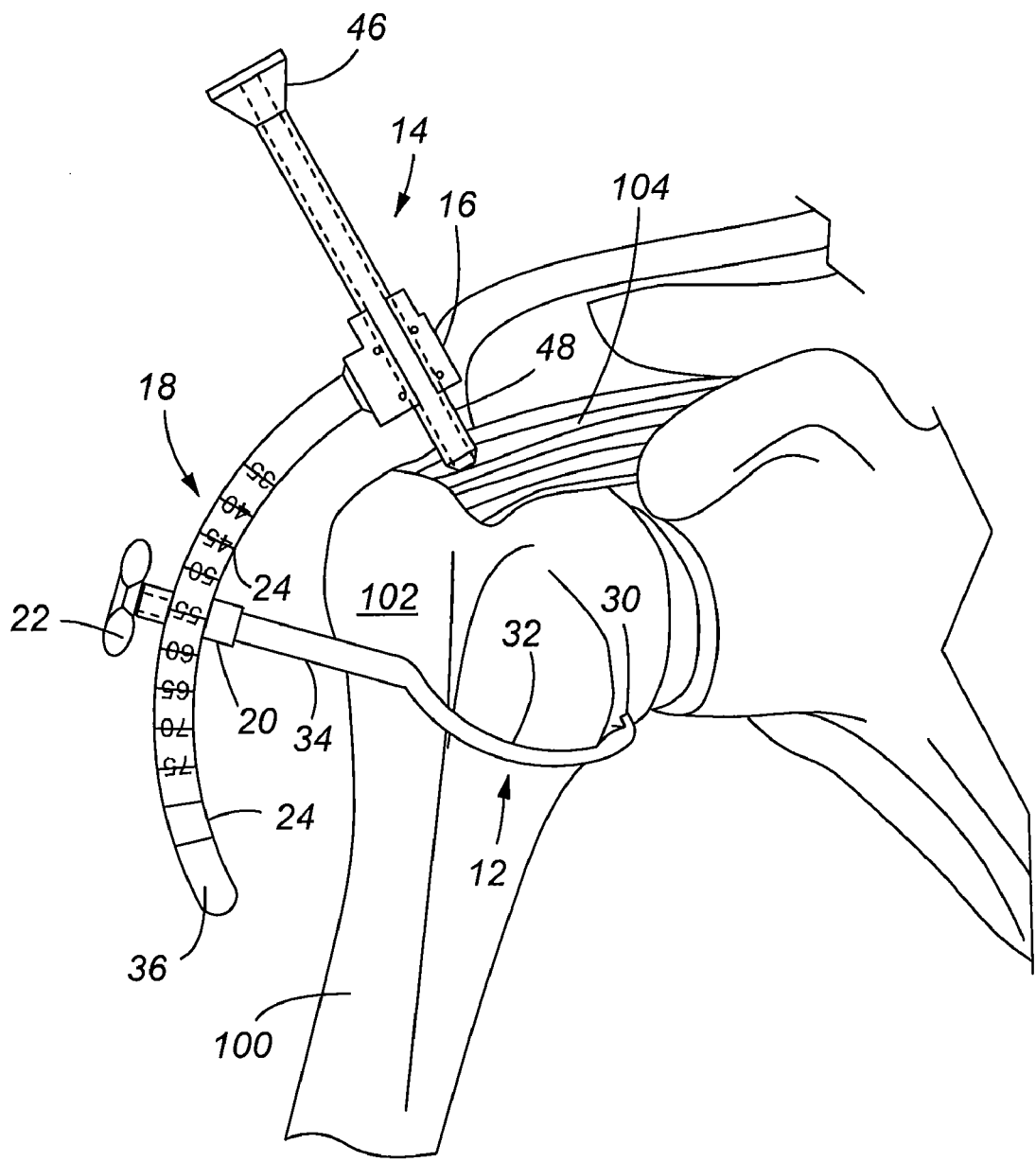
FIG. 4 is a perspective view of the drill guide assembly positioned for use in a surgical procedure for repair of a torn rotator cuff.

Referring to FIG. 4, the drill guide of the present invention is illustrated as it is positioned for use in a rotator cuff repair. To conduct the repair, first the rotator cuff is held in position, such as by a conventional tissue grasping tool (not shown) that has been inserted through the skin and deltoid muscle of the patient to reach the rotator cuff. Once the rotator cuff is in place, then the drill guide of the present invention can be positioned. The practitioner may first locate the marking hook 12 to the desired position on the far cortex of the humeral head by inserting the marking hook through the tissue in the patient and placing the tip 30 on the desired exit point on the far cortex. The practitioner may then position the distal end 44 of the drill guide 14 on the selected location where the practitioner desires to drill the tunnel. The distal end 44 of the drill guide is then passed through the skin, deltoid muscle, and rotator cuff to contact with the humeral head.

The practitioner drills a first bone tunnel by inserting the drill 60 through the bore 80 to drill the bone tunnel. The drill bit tip 66 exits the far end of the cortex and is placed directly adjacent the hook point 30. The marking hook 12 is then manipulated to insert the hook point 30 through the aperture 74 in the drill bit tip 66. The drill shaft 62 is then unscrewed from the drill bit tip 66 thereby leaving the drill bit tip 66 in place as attached to the hook point 30. The use of a cannulated marking hook and drill guide for passing of a relay material can facilitate the passing of sutures. A cannulation running down the length of the marking hook allows the surgeon to pass the relay material to the exit site of the drill. This method and physical guide would allow the surgeon to pass suture to the new tunnel placement and allow for a grasper to be used down the bone tunnel (and possibly the drill guide) to retrieve the suture in sequential steps. The drill guide can have multiple drilling bores to accommodate different spacing for adjacent bone tunnels and can still incorporate the use of the same marking hook.

Referring to FIG. 5, the first bone tunnel 86 is illustrated extending through the humeral head. At this point, the practitioner may pass one or more sutures 88 through the bone tunnel 86. Referring also to FIG. 6A, the sutures 88 are passed through the bone tunnel, through the aperture 74 in the drill bit tip, and then are secured to the drill bit tip 66 as by a knot 89 that is tied. As shown in FIG. 6A, the drill bit tip 66 is located on the bare area 110 on the humeral head 102 and extends transversely across the opening in the bone tunnel to prevent the tip 66 from being pulled back through the tunnel. Accordingly, the length of the tip 66 is preferably longer than the diameter of the tip so the tip can be used as the transversely placed anchor. By this procedure, the drill bit tip serves the dual purpose of drilling the bone tunnel and as the anchor. The opposite ends of the sutures can be attached to the soft tissue around the rotator cuff, such as by soft tissue anchors 84.

FIG. 6B illustrates a modified drill bit tip 66 having a pair of apertures 74. In another method of repair as shown in this Figure, the sutures are passed through the tunnel, through one aperture 74, back through the other aperture 74, and then back through the tunnel so that the free ends of the sutures are all tied along the superior aspect of the greater tuberosity. Thus, there are no knots located at the tip/anchor 66 that further simplifies the procedure by only requiring suture knots/arrangements at the more easily viewed position along the superior aspect of the greater tuberosity.

Figure 7:
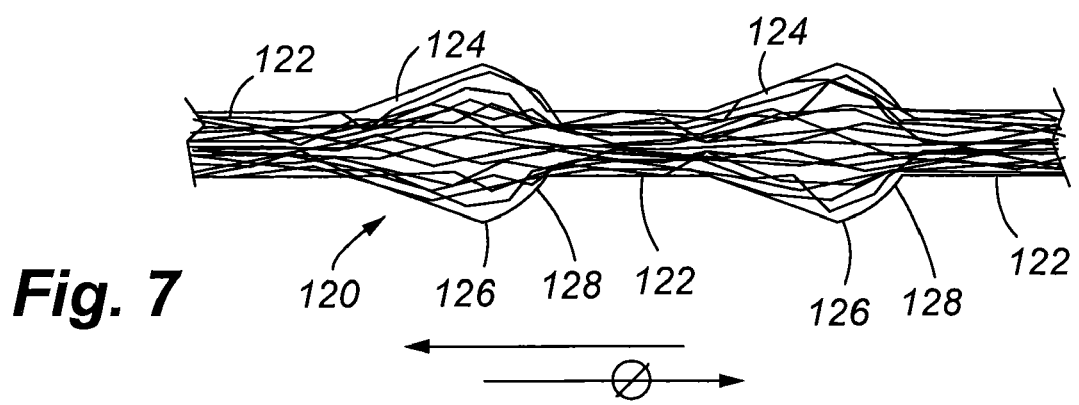
FIG. 7 is a greatly enlarged perspective view of a suture especially adapted for use in the apparatus and method of the present invention.

Referring to FIG. 7, in accordance with another aspect of the present invention, a suture 120 is provided that is especially adapted for use in securing sutures in place thereby minimizing staples and other hardware. As shown in FIG. 7, the suture 120 comprises a plurality of fibers woven together to form unexpanded portions 122 interspersed with a plurality of expanded portions 124. The expanded portions are characterized by a head or protuberance 126, a gradual sloping front edge, and a more sharply narrowing back edge 128. The expanded portions are formed by separating or pulling the strands of material apart from the more tightly woven group of fibers in the unexpanded portions 122. The head or protuberance 126 is tapered with respect to the longitudinal axis of the suture 120.

As shown with the directional arrows, the suture can be passed through the bone tunnel or tissue in the direction from right to left as shown in FIG. 7; however, the suture incorporates a grasping feature which prevents pullout in the direction from left to right. This grasping feature is achieved by the geometry of the suture in which the heads 126 engage the interior surface of the bone tunnel to prevent movement of the suture from within the bone tunnel. This pullout or anchoring feature therefore allows a practitioner to incorporate the suture through the bone tunnel and increase frictional resistance of the suture in the bone tunnel that therefore minimizes the forces transmitted to both the anchor 66, as well as the hardware used to secure the sutures over the deltoid muscle after the procedure has taken place. The diameter of the suture can be chosen to match the bone tunnel to be drilled so that optimal frictional resistance is achieved between the suture and the bone tunnel.

Figure 8:
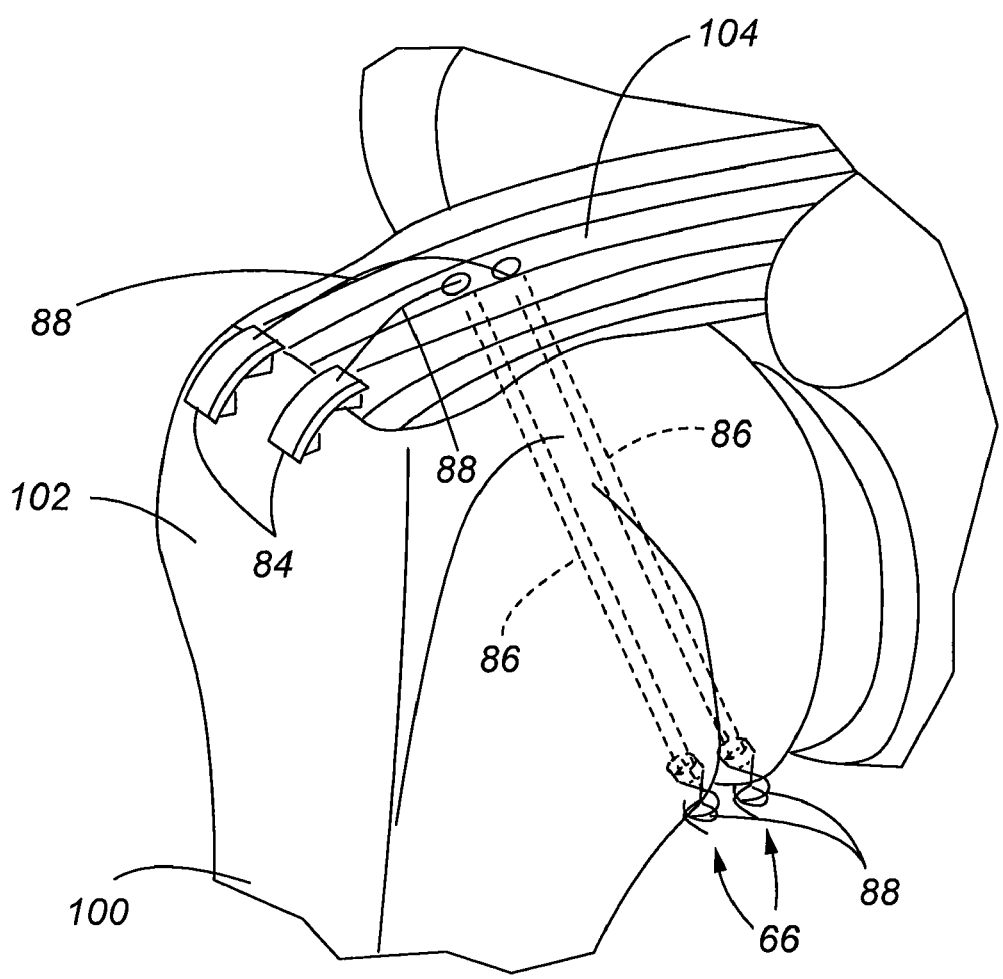
FIG. 8 is another greatly enlarged fragmentary perspective view of a patient's shoulder area illustrating a pair of bone tunnels, and pairs of accompanying hardware to include corresponding bone anchors and soft tissue anchors.

Referring to FIG. 8, a rotator cuff repair is illustrated with reference to a pair of bone tunnels 86, and a corresponding pair of suture groups, drill bit anchors 66, and soft tissue anchors 84. It shall be understood that the practitioner has the option of creating the requisite number of bone tunnels and suture configurations in order to repair the particular rotator cuff injury.

In accordance with another method of the present invention, the sutures can be passed through one or more bone tunnels after being secured along the far cortical bone, then passed through the cuff, tied over the cuff tendon, and then passed through one or more additional bone tunnels along the lateral aspect of the greater tuberosity back to the far cortical bone.

One particularly challenging type of rotator cuff repair is the repair of a partial thickness cuff tear. An in situ repair can be accomplished with the drill guide of the present invention by placing the drill guide 14 on top of the tear, passing the drill bit through the tendon, passing the sutures through the transosseous tunnels and tying knots on top of the tendon. As understood by the skilled surgeon, it is very difficult to pass an anchor across the partially intact cuff since the landmarks are hidden from arthroscopic view. The emplacement of the marking hook on the tear therefore obviates the need to see the tuberosity and provides a precise aiming point for the drill without further imaging and without further incisions made to view the landmarks.

Figure 9:
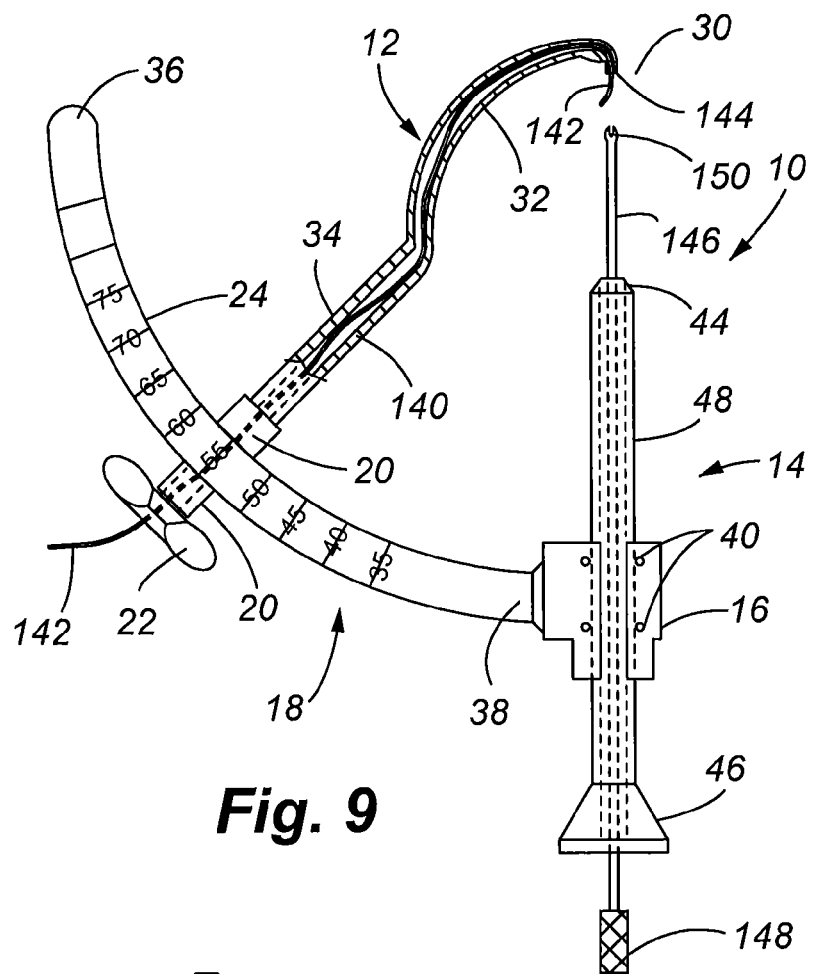
FIG. 9 is a plan view of a drill guide assembly and a cross sectional view of a cannulated marking hook of the assembly in another embodiment of the present invention.

FIG. 9 illustrates a modification to the drill guide assembly 10, which includes a cannulated marking hook 12 characterized by a continuous orifice that extends through the marking hook 12. The marking hook 12 as shown also includes a suture 142 that passes through the orifice 140, such that one end of the suture 142 extends through an opening 144 that communicates with the orifice 140. FIG. 9 also illustrates a grasping tool 146 having a handle 148 allowing the practitioner to grasp one end of the tool and insert it through the opening in the drill guide 14. Grasping tines 150 located at the distal tip of the tool 146 can then grasp the protruding end of the suture 142, so that it may be passed through the bone tunnel for purposes of suturing the tissue to be repaired in the surgical procedure.

Also in reference to FIG. 9, the cannulated marking hook 12 allows for any other type of relay material to be passed adjacent the exit point of the drill, such as PDS or nitinol wire. The close proximity of the exit point of the drill therefore allows for a blind retrieval of the relay material and subsequent suture passing, with a minimized need for visualizing the area. In other words, because the drill tip will intersect the marking hook tip, use of a tool like the illustrated grasping tool 146 allows a practitioner to easily retrieve relay material in somewhat of a blind fashion which thereby greatly eases in the commencement of the suture passing.

Figure 10:
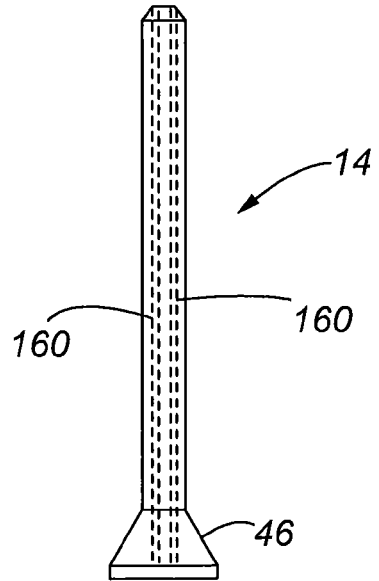
FIG. 10 is a plan view of an alternate embodiment for a drill guide of the drill guide assembly wherein the drill guide includes a pair of offset bores.

FIG. 10 illustrates a modified drill guide 14 including a pair of bores 160. This dual set of bores within the drill guide 14 allow the practitioner additional options in setting offset distances to accommodate different drill positions to address different rotator cuff tear patterns.

Figure 11:
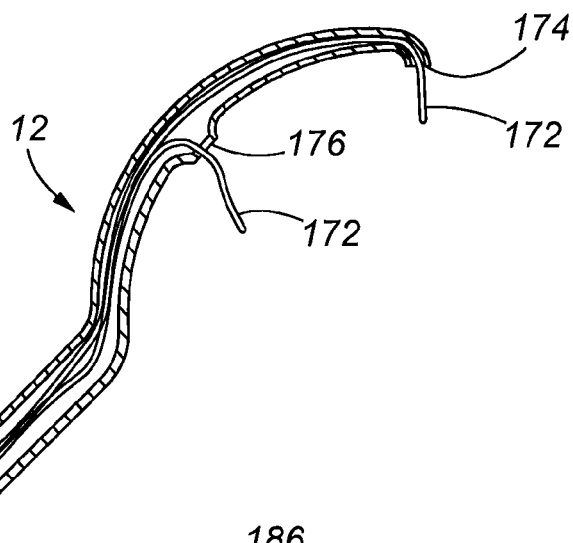
FIG. 11 is a cross sectional view of another embodiment of a cannulated marking hook of the drill guide assembly.

Referring to FIG. 11, another modification is shown to the marking hook 12. This modification includes two separate orifices 140 that extend completely through the marking hook 12. One of the orifices 140 terminates at intermediate opening 176. The other orifice terminates at distal opening 174. As also shown in the figure, two sets of sutures 172 extend through the orifices 140. A marking hook having multiple offset ending points at the openings 174 and 176 allows for convenient relay retrieval at different designated offset aiming points. For example, there may be multiple bone tunnels formed through the humeral head, and it may be necessary to relay sutures through each of the bone tunnels. The openings 174 and 176 may be centered over the bone tunnels previously drilled, which therefore allows for convenient relay retrieval without having to reposition the marking hook numerous times.

Figure 12:
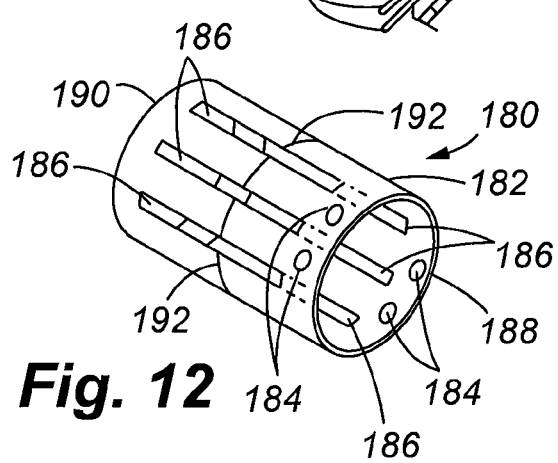
FIG. 12 is a greatly enlarged perspective view of an implantable anchor in another aspect of the present invention.
Figure 13:
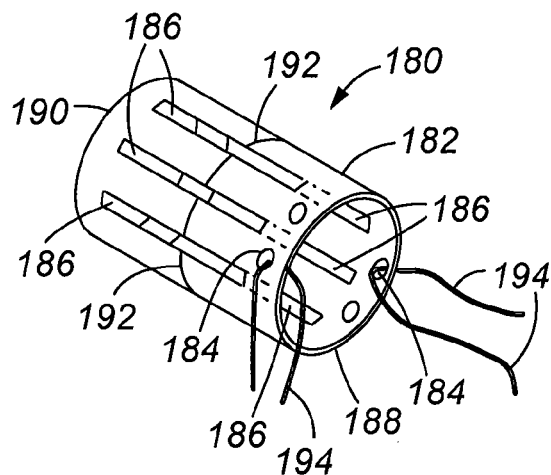
FIG. 13 is another perspective view of the implantable anchor of FIG. 12, illustrating sutures attached to the implantable anchor.

Referring to FIGS. 12 and 13, in another aspect of the invention, an implantable anchor is provided that can be used to anchor sutures, such as those that extend through a bone tunnel. The implantable anchor 180 includes a cylindrical shaped body/cage 182, and a plurality of circumferentially spaced and longitudinally extending slits or openings 186. Approximately midway between the distal end 188 and the proximal end 190 of the anchor is a weakened area forming a score line 192. Adjacent the distal end 188 of the anchor are a plurality of openings 184 that receive one or more sutures 194, as shown in FIG. 13.

Figure 14:
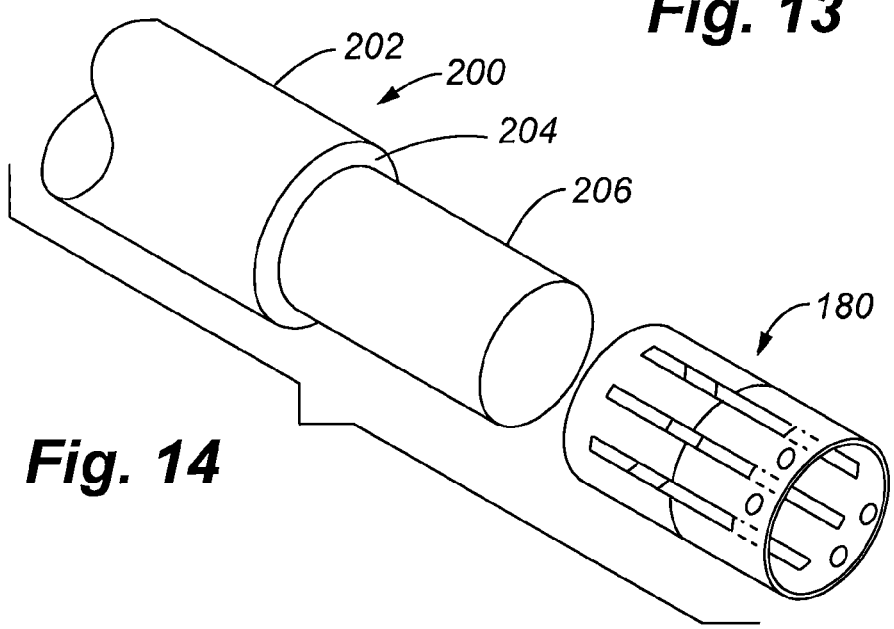
FIG. 14 is a perspective view of an emplacement tool and the implantable anchor.

Referring to FIG. 14, an inserting tool 200 is shown that is used to emplace the anchor 180. The inserting tool 200 includes a proximal body 202, a distal tip 206 having a diameter which is less than the body 202, as defined by the shoulder 204 which delineates the distal end of the body 202 and the proximal end of the tip 206.

Referring also to FIG. 165, the anchor 180 is positioned over the tip 206, and the sutures 194 extend proximally as shown.

Figure 17:
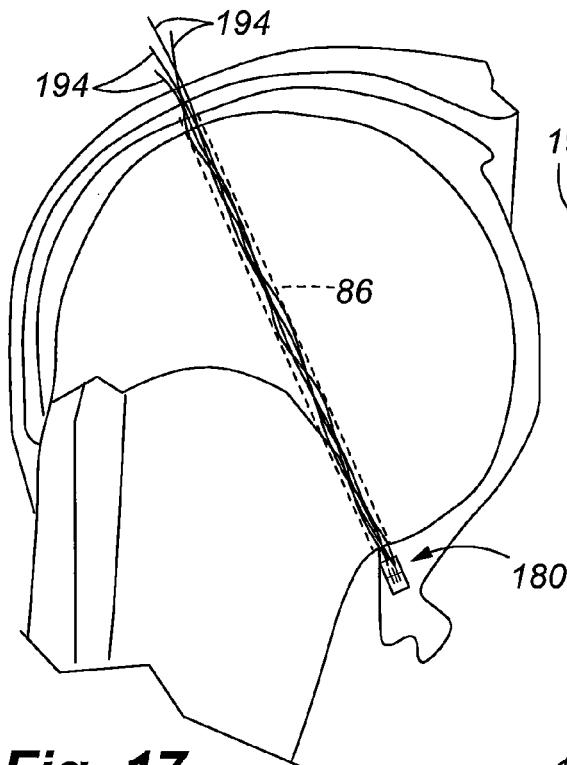
FIG. 17 is an enlarged view of the shoulder area illustrating a bone tunnel, and the implantable anchor passed through the bone tunnel and positioned for attachment to the bare area on the humeral head.

Referring to FIG. 16, the anchor 180 is shown in its mounted position over the tool 200, and the tool 200 is then inserted through the drill guide 14. The tool 200 has a length which accommodates the combined length of the drill guide 14 and bone tunnel 86, so that the anchor 180 can be placed completely through the bone tunnel and beyond the far side of the joint, as shown in FIG. 17. Once the anchor 180 has cleared the bone tunnel, the anchor can be activated to secure the sutures. One method of employment of the anchor is to keep the anchor 180 mounted over the tool 200 as explained below with respect to FIGS. 180A through 18C. Another method of employment is to release the tool 200 from engagement with the anchor 180 after the anchor 180 has passed through the bone tunnel, as also explained below.

Figure 18A:
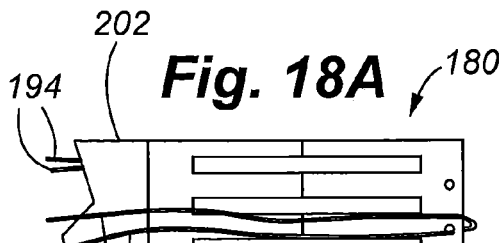
FIG. 18A illustrates the implantable anchor mounted over the tool prior to expansion of the anchor.
Figure 18B:
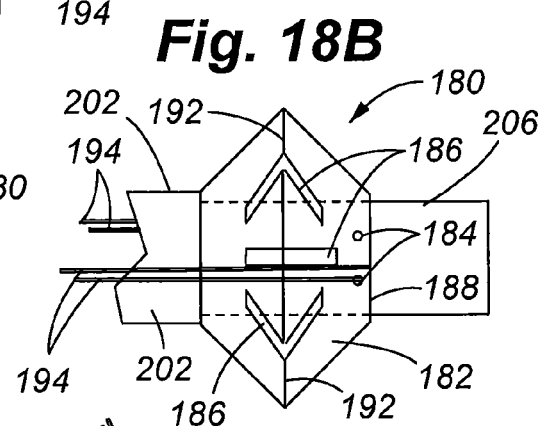
FIG. 18B illustrates the implantable anchor as it is deployed.
Figure 18C:
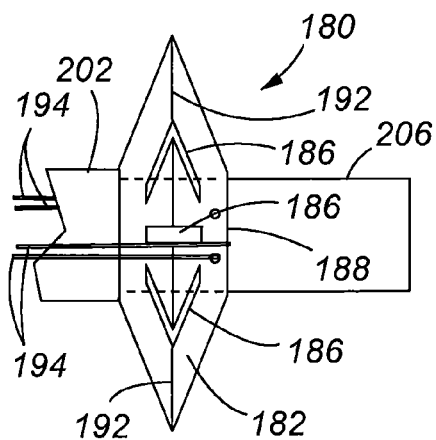
FIG. 18C is another illustration of the implantable anchor as fully deployed.

In order to deploy the anchor 180, the practitioner will pull proximally on the sutures 194 thereby placing them in tension, and causing the anchor 180 to collapse along the score line 192. As shown in FIG. 18A, the sutures are initially without tension, and then tension is placed upon them as shown in FIG. 18B causing the collapse of the anchor. Referring to FIG. 18C, tension is continually applied to fully collapse the anchor along the score line 192. As the anchor collapses, it increases in overall diameter, thereby preventing the anchor 180 from being pulled back through the bone tunnel. Preferably, the diameter of the anchor 180 is just slightly smaller than the diameter of the bone tunnel, such that minimal collapse of the anchor will prevent it from being pulled back through the bone tunnel. The length of the anchor 180 can be approximately 10 mm in length, which will accomplish the necessary anchoring capability for most bone tunnels.

Figure 19:
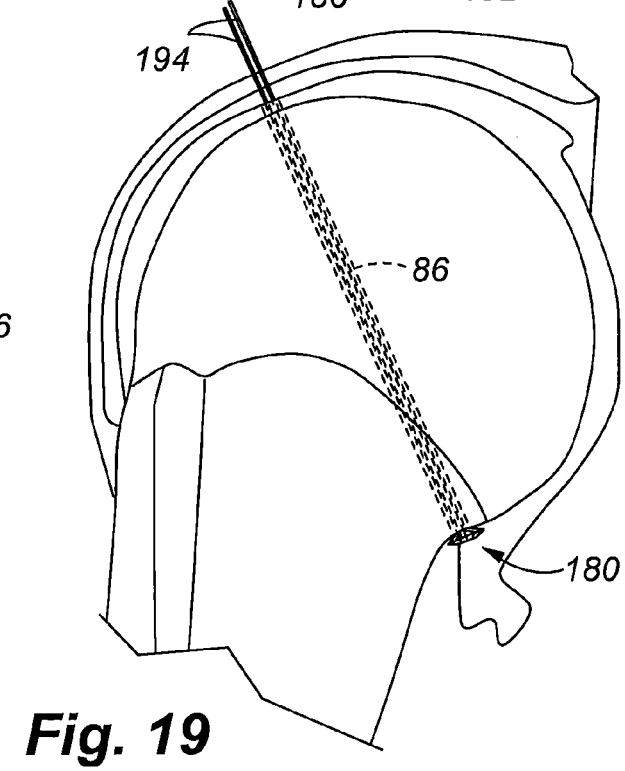
FIG. 19 illustrates the implantable anchor as fully deployed.

As shown in FIG. 19, the anchor 180 has been deployed to its fully collapsed position. The sutures 194 can then be tied/secured at the opposite end of the bone tunnel.

Although only two pairs of sutures 194 are illustrated, additional sutures may be secured through the openings 184 in the anchor 180, depending upon the manner in which the sutures are used for the specific surgical procedure. It is clear from the figures that it is only necessary for one suture 194 for activation/deployment of the anchor 180. It is noted in FIG. 17 that the tool 200 is not illustrated, it being understood that the tool 200 would extend completely through the bone tunnel, and would remain in engagement with the anchor 180 until the anchor was expanded in a diameter to prevent pull back through the bone tunnel 86.

Referring to FIG. 20, in another aspect of the invention, a suture construction is provided in the form of a mesh canopy 222 that can be initially retained on a conventional suture 220.

As shown in FIG. 21, the mesh canopy 222 can be unfurled from a rolled position about the supporting suture 220. The mesh canopy 222 can then be appropriately positioned over the damaged tissue in order to provide a much larger area for support, as compared to a conventional suture arrangement.

As shown in FIG. 22, once the mesh canopy 222 has been deployed, it may extend away from the supporting suture 220 in a fashion to provide greater coverage over a targeted area. A plurality of openings 224 may be formed around the edge of the mesh canopy 222, and these openings 224 may receive a desired set of sutures 226 that may pass through bone tunnels formed in the joint, as shown in FIG. 23.

In the example of FIG. 23, there are four bone tunnels that have been provided through the bone structure, and the pairs of sutures 226 extend in a looped fashion through adjacent pairs of the bone tunnels. The sutures 226 can then be secured over the mesh 222 as by use of securing knots 228. Optionally, the supporting suture 220 may also be secured to the tissue as by tissue anchors 84.

It is clear from the present invention that an effective repair of a rotator cuff injury can be achieved that minimizes traditional bone anchors, and rather incorporates a minimal amount of hardware and simplifies suture arrangements.

Thus, in accordance with the present invention, a rotator cuff repair can be achieved where anchoring of the sutures avoids the cancellous bone mass located beneath the near cortex of the bone in favor of anchoring the sutures at the far cortex of the bone that has a higher bone density. By the use of an especially adapted marking hook, the bone tunnels can be very precisely determined enabling more than one bone tunnel to be created through the bone mass in order to handle the particular rotator cuff injury at hand. Separate bone anchors are replaced in favor of anchoring sutures by the drill bit tip 66 on the far cortex.

Also in accordance with the present invention, unique suture constructions are provided that provide a practitioner with many options for stabilizing torn tissue to include minimizing the stresses produced on bone and soft tissue anchors. A unique anchor is also provided that can be deployed without the use of further instruments, and which is introduced directly through the bone tunnels.

Furthermore, the method of the present invention can be achieved with a minimum of instruments thereby making the procedure of the present invention more susceptible to repeatability and reliability.

While the present invention has been described with respect to preferred embodiments in accordance with the apparatus and method of the present invention, various other changes may be made within the scope of the claims appended hereto.

What is claimed is:

1. A method of arthroscopic repair of a rotator cuff using a bone drill having a drill shaft and a removable drill bit tip, said method comprising:
    positioning the bone drill relative to the rotator cuff and a humeral head;
    drilling a bone tunnel through the humeral head with the bone drill, the bone tunnel extending between a first end of the bone tunnel and a second end of the bone tunnel opposite to the first end;
    disengaging the drill bit tip from the drill shaft and positioning the drill bit tip at the second end of the bone tunnel;
    passing a suture through the bone tunnel such that the suture extends between the first end and the second end;
    securing a first portion of the suture to an aperture formed in the drill bit tip positioned at the second end of the bone tunnel; and
    securing a second portion of the suture relative to the rotator cuff proximate to the first end of the bone tunnel.

2. The method of claim 1, further comprising:
    positioning a drill guide assembly relative to the humeral head for guiding the bone drill; and
    inserting the bone drill through a drill guide in the drill guide assembly for drilling the bone tunnel through the humeral head.

3. The method of claim 2, further comprising, securing the drill bit tip with a marking hook extending from the drill guide assembly prior to disengaging the drill bit tip from the drill shaft.

4. A method of arthroscopic repair of a rotator cuff using a drill guide assembly having a marking hook, an angular setting arm, and a drill guide, said method comprising:
    positioning the drill guide assembly for drilling a hole through a humeral head;
    inserting a bone drill having a drill shaft and a removable drill bit tip through the drill guide;

drilling a bone tunnel through the humeral head with the bone drill, the bone tunnel extending between a first end of the bone tunnel and a second end of the bone tunnel opposite to the first end;

securing the drill bit tip with a distal end of the marking hook;

disengaging the drill bit tip from the drill shaft and positioning the drill bit tip at the second end of the tunnel;

passing a suture through the bone tunnel such that the suture extends between the first end and the second end; and securing a first portion of the suture to an aperture formed in the drill bit tip positioned at the second end of bone tunnel; and securing a second portion of the suture relative to the rotator cuff proximate to the first end of the bone tunnel.

5. The method of claim 4, further comprising, securing the drill bit tip with the marking hook before disengaging the drill bit tip from the drill shaft.

6. The method of claim 4, wherein passing a suture through the bone tunnel further includes passing a suture through an orifice extending through a marking hook to a distal opening at the mounting hook to align the suture at the bone tunnel.

7. A method of arthroscopic repair of a rotator cuff, said method comprising:
providing a drill guide assembly including a marking hook, an angular setting arm, and a drill guide;
positioning the drill guide assembly for drilling a bone tunnel through a humeral head;
providing a bone drill having a drill shaft and a removable drill bit tip;
inserting the bone drill through the drill guide;
drilling a bone tunnel entirely through the humeral head with the bone drill, the bone tunnel extending between a first end of the bone tunnel and a second end of the bone tunnel opposite to the first end;
disengaging the drill bit tip from the drill shaft and positioning the drill bit tip at the second end of the tunnel;
securing the drill bit tip with the marking hook;
passing a suture through the bone tunnel such that the suture extends between the first end and the second end; and
securing a first portion of the suture to an aperture formed in the drill bit tip positioned at the second end of the bone tunnel; and
securing a second portion of the suture relative to the rotator cuff proximate to the first end of the bone tunnel.

8. The method of claim 7, wherein positioning the drill guide assembly further includes positioning the marking hook on a far cortex of the humeral head and positioning a distal end of the drill guide on a selected location opposite the marking hook adjacent the rotator cuff.

9. The method of claim 7, further comprising, passing a distal end of the drill guide through skin, deltoid muscle and rotator cuff to contact the humeral head and thereafter inserting the bone drill through the drill guide.

10. The method of claim 7, further comprising, securing the drill bit tip with the marking hook before disengaging the drill bit tip from the drill shaft.

11. The method of claim 7, wherein securing the drill bit tip with the marking hook further includes manipulating the marking hook to insert a hook point through the aperture formed in the drill bit tip.

12. The method of claim 7, wherein securing the first portion of the suture through the aperture of the drill bit tip includes looping the end back through a second aperture in the drill bit tip.

13. The method of claim 7, further comprising, passing a relay through an orifice of the marking hook to pass the suture through the orifice of the marking hook.

14. The method of claim 7, further comprising:
positioning the drill guide assembly at a second location on the humeral head;
drilling a second bone tunnel through the humeral head with a second bone drill having a second drill shaft and a second removable drill bit tip;
passing a second suture through the second bone tunnel; and
securing an end of the second suture through an aperture formed in a second drill bit tip and securing an opposite end of the suture relative to the rotator cuff.

15. The method of claim 14, wherein passing the second suture through the second bone tunnel further includes passing the second suture through an orifice extending through the marking hook to a distal opening at the marking hook into the second bone tunnel; and
wherein passing a second suture through the second bone tunnel further includes passing the second suture through the orifice extending through the marking hook and out an intermediate opening in the marking hook into the second bone tunnel.

16. The method of claim 7, wherein passing the suture through the bone tunnel further includes passing the suture through an orifice extending through the marking hook.

17. The method of claim 16, further comprising, passing a grasping tool through the drill guide and using grasping tines located at a distal tip of the tool to grasp a protruding end of the suture at the orifice of the marking hook.

18. The method of claim 7, wherein passing the suture through the bone tunnel further includes passing the suture formed of a plurality of woven fibers having a plurality of interspersed expanded portions, wherein the expanded portions increase frictional resistance of the suture in the bone tunnel to minimize forces transmitted to the drill bit tip.

19. The method of claim 7, wherein securing the second portion of the suture includes securing a soft tissue anchor to the second portion of the suture.

20. The method of claim 7, wherein inserting the bone drill through the drill guide further includes, selecting one of a pair of bores extending through the drill guide and inserting the bone drill through the selected bore to drill the bone tunnel at an offset distance relative to the drill guide.

21. The method of claim 7, further comprising:
unfurloughing from the suture a mesh canopy rolled about the suture; and
positioning the mesh canopy over a damaged tissue area of the rotator cuff.

* * * * *

UNITED STATES PATENT AND TRADEMARK OFFICE
CERTIFICATE OF CORRECTION

| | |
|---|---|
| PATENT NO. | : 8,277,458 B2 |
| APPLICATION NO. | : 12/358953 |
| DATED | : October 2, 2012 |
| INVENTOR(S) | : David J. Schneider |

It is certified that error appears in the above-identified patent and that said Letters Patent is hereby corrected as shown below:

In the Claims:

Column 11, Line 42, Claim 7
After "second end" delete "and"

Signed and Sealed this
Fourteenth Day of May, 2013

Teresa Stanek Rea
*Acting Director of the United States Patent and Trademark Office*